US008815385B2

(12) United States Patent
Fearing et al.

(10) Patent No.: US 8,815,385 B2
(45) Date of Patent: *Aug. 26, 2014

(54) CONTROLLING PEEL STRENGTH OF MICRON-SCALE STRUCTURES

(75) Inventors: Ronald Fearing, Orinda, CA (US); Kellar Autumn, Portland, OR (US)

(73) Assignees: The Regents of the University of California, Oakland, CA (US); Lewis & Clark College, Portland, OR (US)

( * ) Notice: Subject to any disclaimer, the term of this patent is extended or adjusted under 35 U.S.C. 154(b) by 1694 days.

This patent is subject to a terminal disclaimer.

(21) Appl. No.: 11/143,372

(22) Filed: Jun. 1, 2005

(65) Prior Publication Data

US 2006/0078725 A1    Apr. 13, 2006

Related U.S. Application Data

(63) Continuation-in-part of application No. 10/655,271, filed on Sep. 3, 2003, now Pat. No. 7,229,685, which is a continuation of application No. 09/644,936, filed on Aug. 23, 2000, now Pat. No. 6,737,160.

(60) Provisional application No. 60/172,731, filed on Dec. 20, 1999.

(51) Int. Cl.
*B32B 5/16*      (2006.01)
*B41M 5/00*     (2006.01)

(52) U.S. Cl.
USPC ........................................ 428/323; 428/195.1

(58) Field of Classification Search
USPC ............... 424/65; 156/60; 428/343; 430/330; 510/190; 24/442
See application file for complete search history.

(56) References Cited

U.S. PATENT DOCUMENTS

| 4,545,831 | A | | 10/1985 | Ornstein |
| 4,704,745 | A | * | 11/1987 | Reaver ............................. 2/268 |
| 5,264,722 | A | | 11/1993 | Tonucci et al. |
| 5,392,498 | A | | 2/1995 | Goulait et al. |
| 5,554,146 | A | * | 9/1996 | Niederhofer et al. ......... 604/391 |
| 5,693,401 | A | * | 12/1997 | Sommers et al. ............. 428/100 |
| 5,755,913 | A | * | 5/1998 | Liaw et al. ................. 156/272.6 |

(Continued)

FOREIGN PATENT DOCUMENTS

| WO | WO-99/32005 | 7/1999 |
| WO | WO-01/49776 | 7/2001 |
| WO | WO-03/095190 | 11/2003 |

OTHER PUBLICATIONS

Autumn, Kellar et al., (Jun. 8, 2000) "Adhesive force of a single gecko foot-hair," Nature, 405: 681-658.

(Continued)

*Primary Examiner* — Gwendolyn Blackwell
*Assistant Examiner* — Anthony J Frost
(74) *Attorney, Agent, or Firm* — Morrison & Foerster LLP

(57) ABSTRACT

A fabricated microstructure includes a base and one or more nano-structures disposed on one or more portions of the base to adhere to a contact surface. The one or more portions of the base with the one or more nano-structures are located on the base such that, when the one or more nano-structures adhere to the contact surface and an external force is applied to peel the base from the contact surface, the one or more nano-structures in the one or more portions of the base facilitate or resist peeling of the nano-structures from the contact surface.

5 Claims, 15 Drawing Sheets

(56) References Cited

U.S. PATENT DOCUMENTS

| | | | |
|---|---|---|---|
| 5,843,657 | A | 12/1998 | Liotta et al. |
| 5,843,767 | A | 12/1998 | Beattie |
| 5,951,931 | A | 9/1999 | Murasaki et al. |
| 5,959,200 | A | 9/1999 | Chui et al. |
| 6,055,680 | A | 5/2000 | Tolbert |
| 6,393,327 | B1 | 5/2002 | Scribner |
| 6,713,151 | B1 | 3/2004 | Dean et al. |
| 6,872,439 | B2 | 3/2005 | Fearing et al. |
| 2002/0100581 | A1 | 8/2002 | Knowles et al. |
| 2003/0124312 | A1 | 7/2003 | Autumn |
| 2004/0005454 | A1 | 1/2004 | Full et al. |
| 2004/0009353 | A1 | 1/2004 | Knowles et al. |
| 2004/0071870 | A1 | 4/2004 | Knowles et al. |
| 2004/0076822 | A1 | 4/2004 | Jagota et al. |
| 2004/0134045 | A1 | 7/2004 | Poulakis et al. |
| 2005/0181170 | A1 | 8/2005 | Fearing et al. |
| 2006/0005362 | A1 | 1/2006 | Arzt et al. |

OTHER PUBLICATIONS

Cartmill, Matt (1985) "Chapter 5: Climbing," in *Functional Vertebrate Morphology*, M. Hildebrand et al. eds., Belknap Press of Harvard University Press, Cambridge, MA, pp. 73-88.

Edwards, John S. (Oct. 1962) "Observations on the development and predatory habit of two *reduviid heteroptera, phinocoris Carmelita stal* and *platymeris rhadamanthus* gerst" Proc. R. Ent. Soc. Lond., 37(7-9): 89-98.

Edwards, John S. et al., (1970) "The adhesive pads of Heteroptera: a re-examination," Proc. R. ent. Socl. Lond. 45(1-3): 1-5.

Hora, Sunder Lal (1923) "The Adhesive Apparatus on the Toes of certain Geckos and Tree-frogs," Journal of the Asiatic Society of Bengal 9: 137-145.

Irschick, Duncan J. et al., (1996) "A comparative analysis of clinging ability among pad-bearing lizards," Biological Journal of the Linnean Society, 59: 21-35.

Janra (Oct. 18, 2002) "Gecko feet in-hair-ently sticky (Science)," <http://www.kuro5shin.org/?op=displaystory;sid=2002/10/18/03840/81 6>, printed Nov. 17, 2005, 12 pages.

Liang, Yiching A. et al., (Jun. 2000) "Adhesion Force Measurements on single Gecko Setae," Technical Digest of the 2000 Solid-State Sensor and Actuator Workshop, Jun. 4-8, 2000, Hilton Head Island, SC, pp. 33-38.

Maderson, P. F. A. (Aug. 15, 1964) "Keratinized Epidermal Derivatives as an Aid to Climbing in Gekkonid Lizards," Nature, 203: 780-781.

Mahendra, Beni Charan, (1941) "Contributions to the Bionomics, Anatomy, Reproduction and Development of the Indian House-Gecko, *Hemidactylus flaviviridis* Ruppel," Proceedings of the Indian Academy of Science, 13(5) Sec. B: 288-306.

Paul, Robert C. et al., (Oct. 21, 1999) "How do flies and other insects walk up walls, ceilings and even apparently smooth glass windows?" <http://www.sciam.com/askexpert_question.cfm?articleID=00053735- 601D-1C72-9EB7809EC588F2D7>, 2 pages.

Peterson, J. A. et al., (Jul. 21, 1981) "A case study in retrograde evolution: the *onca* lineage in anoline lizards. II. Subdigital fine structure," Bulletin of the Museum of Comparative Zoology, 149(4):215-268.

Ruibal, Rodolfo et al., (Nov. 1965) "The Structure of the digital Setae of Lizards," Journal of Morphology, 117: 271-294.

Russell, Anthony P. (1975) "Contribution to the functional analysis of the foot of the Tokay, *Gekko gecko* (Reptilla: Gekkonidae)," Zool Lond., 176: 437-476.

Spice, (Jul. 7, 2003) "Scientists unravel mystery of gecko's sticky feet," post-gazette.com Health & Science, <http://web.archive.org/web/20030709183536/http://www.post-gazette.com/healthscience/ . . . >, printed Nov. 17, 2005.

Stork, N. E. (Oct. 1980) "Experimental analysis of adhesion of *chrysolina polita* (Chrysomelidae: Coleoptera) on a variety of surfaces," J. exp. biol., 88: 91-107.

Stork, N. E., (Mar. 1980) "A scanning electron microscope study of tarsal adhesive setae in the Coleoptera" Zoological Journal of the Linnean Society, 68: 173-306.

Thurn-Albrecht, T. et al., (Dec. 15, 2000) "Ultrahigh-Density Nanowire Arrays Grown in Self-Assembled Diblock Copolymer templates," Science, 290: 2126-2129.

Williams, E. E. (Mar. 19, 1982) "Convergent and Alternative Designs in the Digital Adhesive Pads of Scincid Lizards," Science, 215: 1509-1511.

Non-Final Office Action received for U.S. Appl. No. 11/843,619, mailed on Apr. 19, 2011, 18 pages.

Office Action received for Japanese Patent Application No. 2001-550314, mailed on Apr. 19, 2011, 4 pages (2 pages of English Translation and 2 pages of Office Action).

Office Action received for Japanese Patent Application No. 2001-550314, mailed on Oct. 19, 2010, 8 pages ( 4 pages of English Translation & 4 pages of office Action).

Gasc et al., "Comptes Rendus Des Seances De L'Academie Des Sciences", Serie 3. Sciences de la Vie, vol. 294, No. 3, 1982, pp. 169-174.

Extended European Search Report received for European Patent Application No. 06772042.5, mailed on Mar. 8, 2011, 4 pages.

* cited by examiner

CONTROLLING PEEL STRENGTH OF MICRON-SCALE STRUCTURES

CROSS REFERENCE TO RELATED APPLICATION

The present Application is a continuation-in-part of U.S. patent application Ser. No. 10/655,271, filed Sep. 3, 2003 now U.S. Pat. No. 7,229,685, which is a continuation of U.S. patent application Ser. No. 09/644,936, filed Aug. 23, 2000, now U.S. Pat. No. 6,737,160, which claims the benefit of provisional Application 60/172,731, filed Dec. 20, 1999. All of the previously mentioned Applications are incorporated herein by reference in their entirety.

STATEMENT REGARDING FEDERALLY SPONSORED RESEARCH OR DEVELOPMENT

This invention was made with Government support under contracts 9980838 awarded by the National Science Foundation and N00014-98-C-0183 awarded by the Office of Naval Research through a subcontract from I.S. Robotics. The Government has certain rights in this invention.

BACKGROUND

1. Field

The present application relates generally to the fabrication and utilization of micron-scale structures. More particularly, this application relates to controlling peel strength of micron-scale structures.

2. Related Art

There is an ongoing need for improved adhesives. Improved adhesives have applications ranging from everyday aspects of life (e.g., tape, fasteners, and toys) to high technology (e.g., removal of microscopic particles from semiconductor wafers, transporting fiber optic devices, and assembly of sub-mm mechanisms, particularly those including micro-fabricated components, or components that cannot tolerate grippers, adhesives, or vacuum manipulators).

Adhesive mechanisms in nature have been studied, but have not been fully understood or exploited. For example, Geckos are exceptional in their ability to rapidly climb up smooth vertical surfaces. The mechanism of adhesion used in Geckos, Anolis lizards, some skinks, and some insects, has been debated for nearly a century.

While some prior work has identified the morphology of seta used by Geckos and other insects, this prior work does not identify how the seta operates. In addition, this prior work fails to identify how to use a seta to perform useful work.

It would be highly desirable to identify and exploit the adhesive force mechanism utilized by Geckos and other insects. Such information could result in the utilization of new adhesive microstructures and the fabrication of such structures.

SUMMARY

In one exemplary embodiment, a fabricated microstructure includes a base and one or more nano-structures disposed on one or more portions of the base to adhere to a contact surface. The one or more portions of the base with the one or more nano-structures are located on the base such that, when the one or more nano-structures adhere to the contact surface and an external force is applied to peel the base from the contact surface, the one or more nano-structures in the one or more portions of the base facilitate or resist peeling of the nano-structures from the contact surface.

BRIEF DESCRIPTION OF THE FIGURES

Like reference numerals refer to corresponding parts throughout the drawings.

DETAILED DESCRIPTION

The following description sets forth numerous specific configurations, parameters, and the like. It should be recognized, however, that such description is not intended as a limitation on the scope of the present invention or applications thereof, but instead provides examples and illustrations.

The invention is directed toward the use of micron scale structures to achieve adhesion. In particular, the invention uses a seta structure. The seta structure has a shaft. Positioned at the end of the shaft is a spatula or an array of spatulae. Adhesion is produced as the spatula or array of spatulas produce intimate contact with a surface.

In general, the shaft is between 1 and 500 microns long, preferably approximately 10 to 100 microns long. The diameter of the shaft is preferably between 0.01 and 0.1 times the length of the shaft, preferably approximately 0.05 times the length of the shaft.

The terminal end of the shaft has at least one spatula. Preferably, the terminal end of the shaft has between 1 and 1000 spatulae. The array of spatulae is preferably less than 10 microns wide, preferably approximately 1 micron wide. Preferably, each spatula of the array of spatulae has an extended surface at its terminal end. The extended surface may be in the form of a paddle or a curved segment of a sphere, as shown below.

The structure of the invention is modeled from structures found in nature, such as the seta found on the foot of a Tokay gecko (Gekko gecko). Many species of gecko (e.g., clade Gekkonoidea), species of Anolis, and several skink species have adhesive setae that may also be used in accordance with the invention. In addition, beetles and kissing-bugs have setae that may be used in accordance with the invention. The invention is implemented with natural or fabricated setae, as discussed below.

Examples of seta structures found in nature follow. The seta of a Tokay Gecko has a stalk (shaft) diameter of 5μ, a stalk height of 110μ, a tip (spatulae) length of 0.2μ, a tip width of 0.2μ, and between 100-1000 tips, where the total tip area per stalk is 2 to 20μ$^2$, Anolis cuvieri has a stalk diameter of 0.5μ, a stalk height of 22μ, a tip length of 0.6μ, a tip width of 0.7μ, and between 100-1000 tips, where the total tip area per stalk is 2 to 20μ. Prasinohaema virens (skink) has a stalk diameter of 2μ, a stalk height of 26μ, a tip length of 6μ, a tip width of 7μ, and between 100-1000 tips, where the total tip area per stalk is approximately 20μ.

Figure 1A:
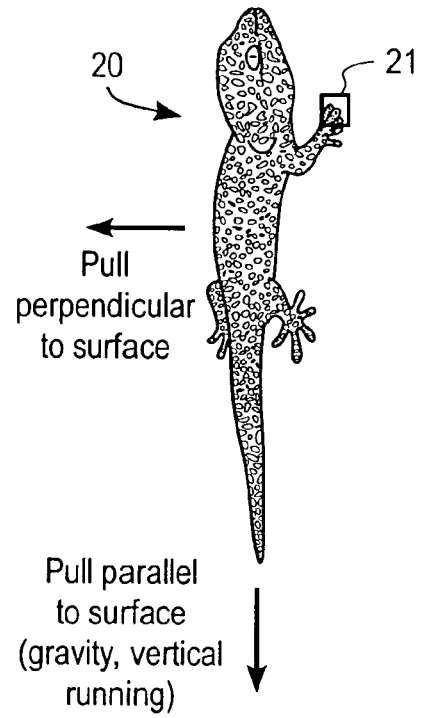
FIG. 1A illustrates preloading operations performed in accordance with an embodiment of the invention.

By way of example, FIG. 1A illustrates a Tokay gecko 20 with terminal limbs 21 that have naturally occurring setae. The live gecko 20 is restrained. The cuticular layer of a portion of a terminal limb (e.g., a toe) 21 is removed. This operation, analogous to cutting hair, allows the gecko to harmlessly regenerate its setae. It has been demonstrated that hundreds or thousands of setae can be easily harvested without sacrificing the living being from which the setae are removed.

Figure 1B:
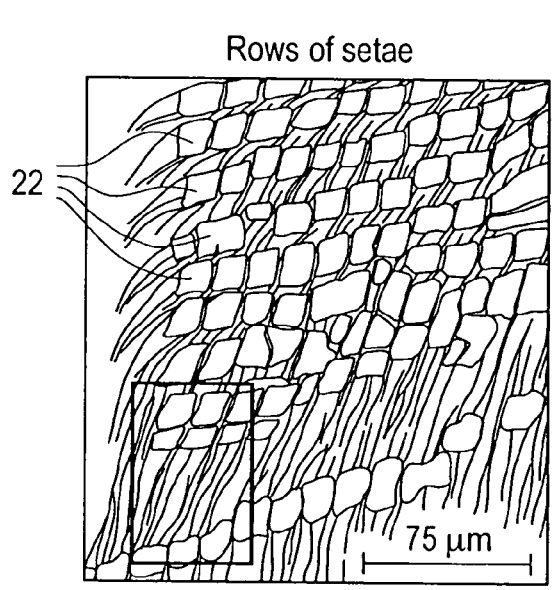
FIG. 1B illustrates rows of setae used in accordance with the invention.
Figure 1C:
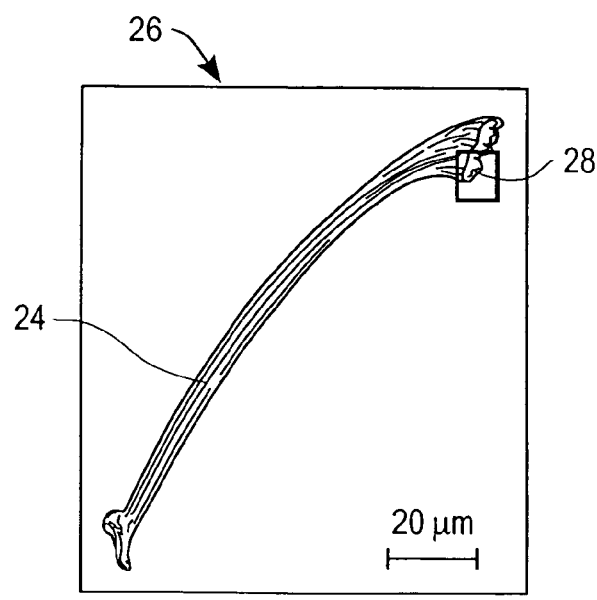
FIG. 1C illustrates a single seta used in accordance with the invention.

After removal, the cuticular surface is scraped to break off individual seta, preferably at the base of the shaft of the seta. FIG. 1B illustrates rows 22 of setae associated with the gecko 20. FIG. 1C illustrates the shaft 24 of a single seta 26. The figure also illustrates the spatulae 28 positioned at the end of the shaft 24.

Figure 1D:
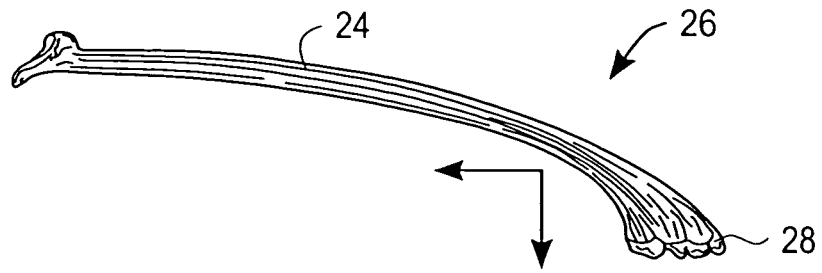
FIG. 1D is an enlarged view of a single seta used in accordance with an embodiment of the invention.

FIG. 1D is an enlarged view of a single seta 26. The figure illustrates that the shaft 24 is roughly perpendicular to the spatulae 28.

Figure 1E:
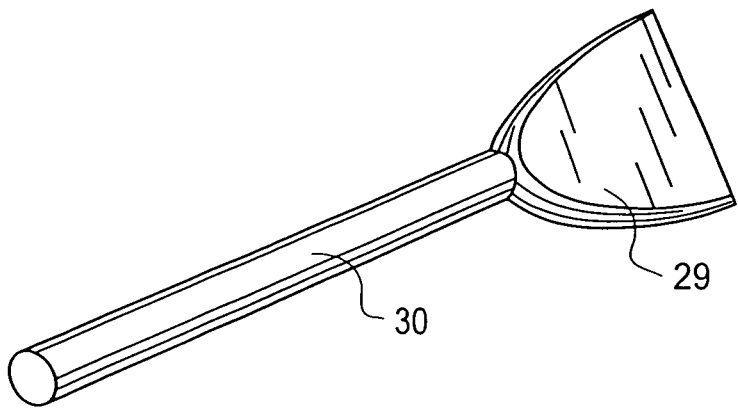
FIG. 1E is an enlarged view of a single extended surface spatula on a spatula stalk, in accordance with an embodiment of the invention.
Figure 1F:
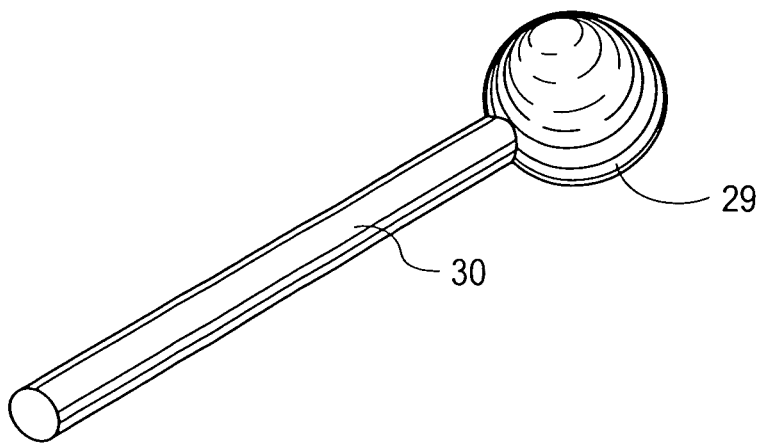
FIG. 1F is an enlarged view of a single extended surface spatula on a spatula stalk, in accordance with an embodiment of the invention.
Figure 1G:
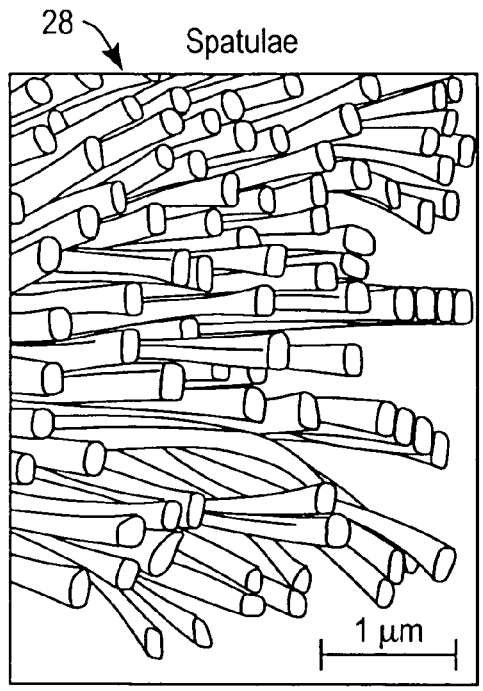
FIG. 1G illustrates an array of spatulae formed at the end of a shaft to form seta used in accordance with the invention.

FIG. 1E is an enlarged view of a single spatula 29 on a spatula stalk 30. The spatula stalk 30 may be the shaft 24 or a separate tendril extending from the shaft 24. Preferably, each spatula 29 has an extended surface. In FIG. 1E, the extended surface is in the form of a paddle structure. In FIG. 1F, the extended surface is in the form of a sphere. FIG. 1G is an enlarged view of an array of spatulae 28.

Figure 1H:
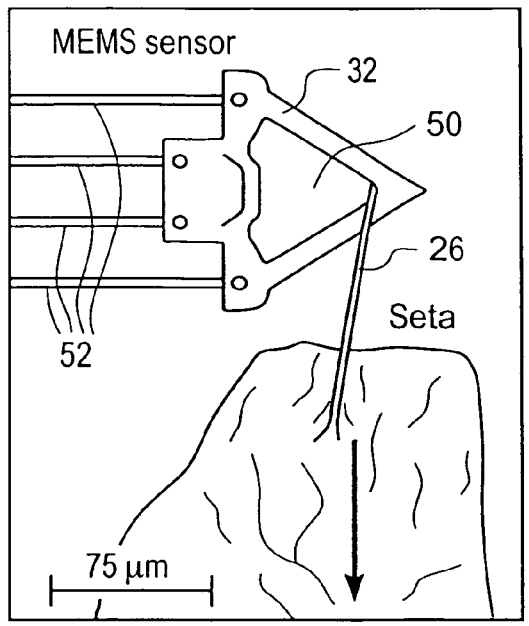
FIG. 1H illustrates a system to measure adhesive force achieved in accordance with the invention.
Figure 1I:
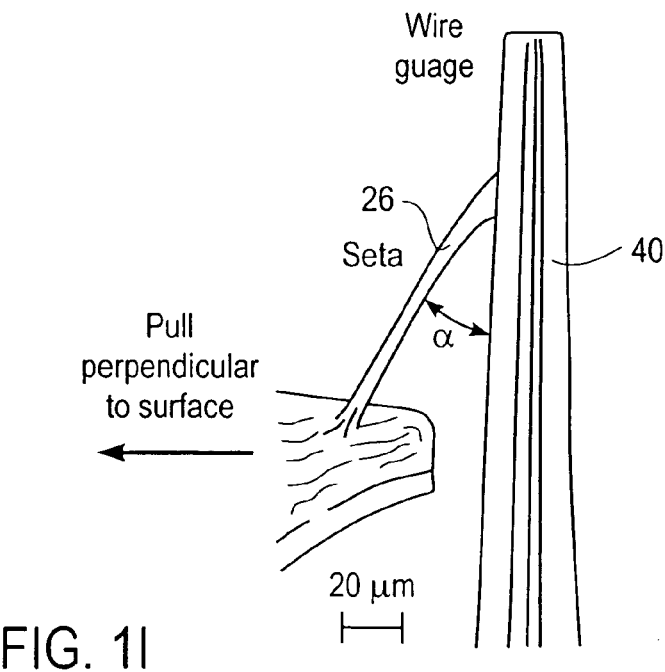
FIG. 1I is another illustration of a system to measure adhesive force achieved in accordance with the invention.

The realization of large adhesive forces by the setae is contingent upon preload operations performed in accordance with the invention. Detachment of the setae occurs at a characteristic angle, as specified in accordance with the invention. FIG. 1H illustrates a substrate (i,e., a sensor 32) that was used to characterize these forces. FIG. 1I illustrates the characteristic angle ($\alpha$) for detaching setae of the invention. The characteristic angle ($\alpha$) is formed between the seta 26 and a surface 40 to which the seta is attached.

The inventors have identified that the adhesive force of a seta depends upon its three-dimensional orientation (spatulae pointing toward or away from the surface) and the extent to which the seta is preloaded (pushed into and pulled along the surface) during initial contact. Contacting the surface with the seta in a direction other than with spatulae projecting toward the surface resulted in forces less than 0.3 μN when the seta was pulled away perpendicular to the surface. A pull parallel to the surface showed that the force produced by the inactive, non-spatular region increased with normal or perpendicular force, typical of a material with a coefficient of friction equal to 0.2. By contrast, when the active spatular region was projecting toward the surface, force increased by 20 to 60-fold. The force resulting from pulling the seta parallel to the surface during attachment increased when setae were first pushed toward the surface, providing a perpendicular preloading force. This initial perpendicular force need not be maintained during the subsequent pull. Setal force parallel to the surface increased linearly with the perpendicular preloading force.

Experiments in which seta were pulled away from the surface of a wire demonstrated that perpendicular preloading alone is insufficient to prevent the seta from being dislodged easily. Seta that were first pushed into the surface and then pulled parallel to it developed over ten times the force (13.6 μN±2.6 SD; N=17) upon being pulled away from the surface than those having only a perpendicular preload (0.6 μN±0.7 SD; N=17). The largest parallel forces were observed only following a few microns of sliding. The results of preloading on setal force production suggest that a small perpendicular preloading force in concert with a rearward displacement or parallel preload may be necessary to "engage" adhesion. Preloading is believed to increase the number of spatulae contacting the surface.

The orientation of the setae is also important in detachment. The force produced when a seta was pulled away from the surface was not significantly differently from the force measured during a pull parallel to the surface if the same perpendicular preload was given However, it has been identified that setae detached at a similar angle (30.6°±1.8 SD; N=17) and force when pulled away from the sensor's surface. To check for the presence of a critical angle of detachment, the perpendicular force was held constant, while the setal angle was progressively increased until detachment. Setal angle at detachment changed by only 15% over a range of perpendicular forces. Thus, the invention utilizes a detachment angle of between 35° and 25°, preferably approximately 30°. The detachment angle values are based upon the disclosed seta structure in which the shaft of the seta is roughly perpendicular to the spatular surface, as shown in FIG. 1D. Change in the orientation of the setae and perhaps even the geometry of the spatulae may facilitate detachment.

The foot of a Tokay gecko (Gekko gecko) holds approximately 5000 setae $mm^{-2}$ and can produce 10 N of adhesive force with approximately 100 $mm^2$ of pad area. Therefore, each seta should produce an average force of 20 μN and an avenge stress of 0.1 N $mm^{-2}$ (~1 atm). The actual magnitudes are probably greater, since it is unlikely that all setae adhere simultaneously.

The foregoing information is more fully appreciated in connection with specific operations performed in accordance with the invention. An isolated seta, secured by the technique discussed above, was glued to a substrate (e.g., to the end of a #2 insect pin) with epoxy (e.g., 5-MINUTE EPOXY sold by TTWDevcon, Danvars, Mass.). The pin had a diameter of approximately 15 μm. To prevent the epoxy from creeping up the stalk of the seta, which might change the mechanical property of the specimen, the epoxy is preferably precured for approximately 1 minute before applying it to the specimen. All setae were oriented such that the active surface was approximately perpendicular to the axis of the pin. All preparations were completed under a compound microscope.

Force production by single, isolated seta during attachment was measured using a micromachined, dual-axis, piezoresistive sensor 32 of the type illustrated in FIG. 1H. The following discussion provides information with respect to the sensor 32. U.S. Pat. No. 5,959,200 describes a sensor of the type described herein. The sensor 32 does not form a part of the invention, rather it is merely used to obtain the performance results described below.

The cantilever sensor 32 of FIG. 1H was fabricated on a single-crystalline silicon wafer. The cantilever 32 has two independent force sensors, each with one predominant direction of compliance. The perpendicular force sensor consists of a thin triangular probe 50. The parallel force sensor is composed of four long slender ribs 52. A special 45° oblique ion implantation allowed piezoresistive and conductive regions to be implanted on both the parallel and perpendicular surfaces simultaneously. Forces applied to the tip of the sensor were resolved into these two orthogonal directions (parallel and perpendicular), and were measured by the changes in resistance of the piezoresistors. Since this device was originally designed for Atomic Force Microscope data storage applications, each of these cantilever devices had a sharp tip near the vertex of its triangular probe. For the gecko setae adhesion measurement, the back-side of this device was used to provide a smooth surface for setal adhesion.

Figure 3:
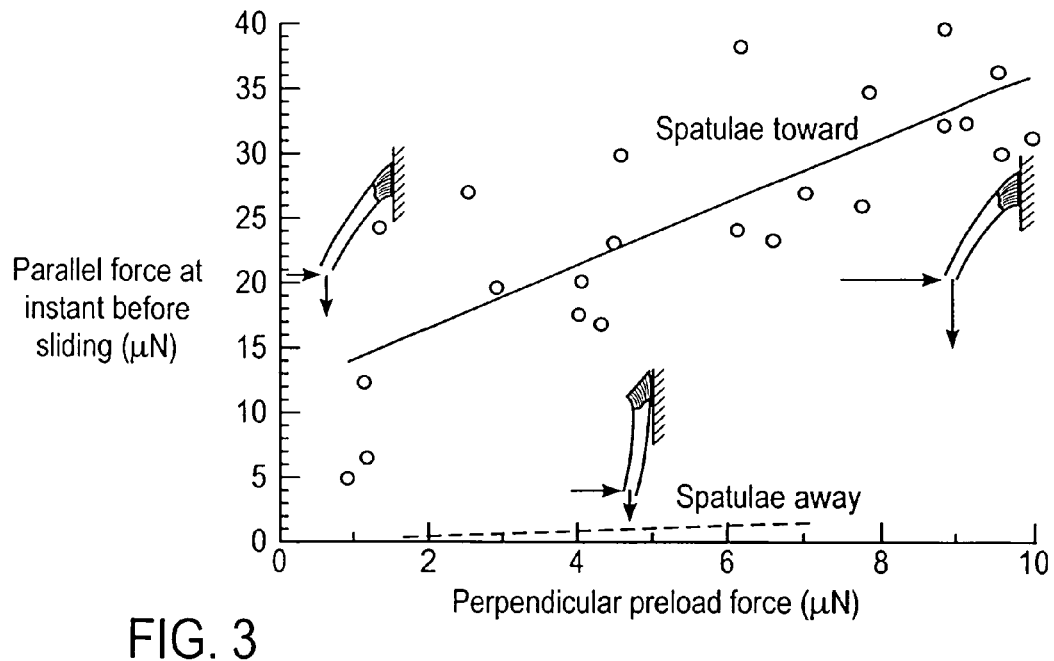
FIG. 3 illustrates perpendicular preload force associated with an embodiment of the invention.

Each sets 26 was brought in contact with the sensor 32 by applying a small preload perpendicular to the surface to increase contact and induce adhesion. To determine the effect of preload force on submaximal parallel force, preload force was varied when setae were attached to the tip of the sensor, as shown in FIG. 3, which is discussed below. To measure maximal parallel force, the base of the triangular probe was used. Using the base increased area of contact, but did not allow for simultaneous measurement of preload forces. Sensor signals were taken while the seta was being pulled parallel to the surface by a piezoelectric manipulator at a rate of ~5 μm $sec^{-1}$. Sensor signals were amplified and filtered through a 300-Hz low-pass filter, and then digitized at 100 Hz using a 16-bit data acquisition card (Lab View™ on a PC). The collected data (in volts) were converted to deflections of the sensor through calibration constants, and multiplied by the stiffness of the cantilever to obtain force values.

Breaking or detachment force was defined as the maximal force a seta could exert perpendicular, or normal, to a surface immediately before it released. This value was determined for individual seta by measuring the amount it could displace a force gauge made from a 4.7 mm aluminum bonding wire with 25 μm nominal diameter (American Fine Wire Corp., Selma, Ala.; the wire 40 is shown in FIG. 1I). To maximize contact area of the active surface of the seta to the wire, a 50 μm.times.100 μm section of the wire tip was flattened. The proximal end of the wire was fixed with epoxy onto a brass stub. The active surface of the seta was pressed against the flattened wire, producing a known perpendicular preload (1.6±0.25 μN; means±SD). The force was measured using two different methods of detachment: (1) the seta was pulled normal to the wire; and (2) the insect pin was displaced 19.7±3.45 μm along the wire to produce an additional parallel preload on the seta before pulling perpendicular or normal to the wire.

In all trials, detachment force was calculated from the maximum displacement of the wire pulled by the seta. All sequences were recorded with a video camera (e.g., a CCD camera sold by SONY) and digitized to a computer (e.g., an APPLE, MACINTOSH) using a video editing system (e.g., from MEDIA 100 Inc., Marlboro, Mass.). The initial position of the wire, the angle of the seta with respect to the wire and the position of the wire at the point of separation were recorded and analyzed using image analysis software (e.g., NIH-Image software). The amount of deflection in the force gauge was converted to adhesion force after the force gauge was calibrated against standard weights.

Figure 2A:
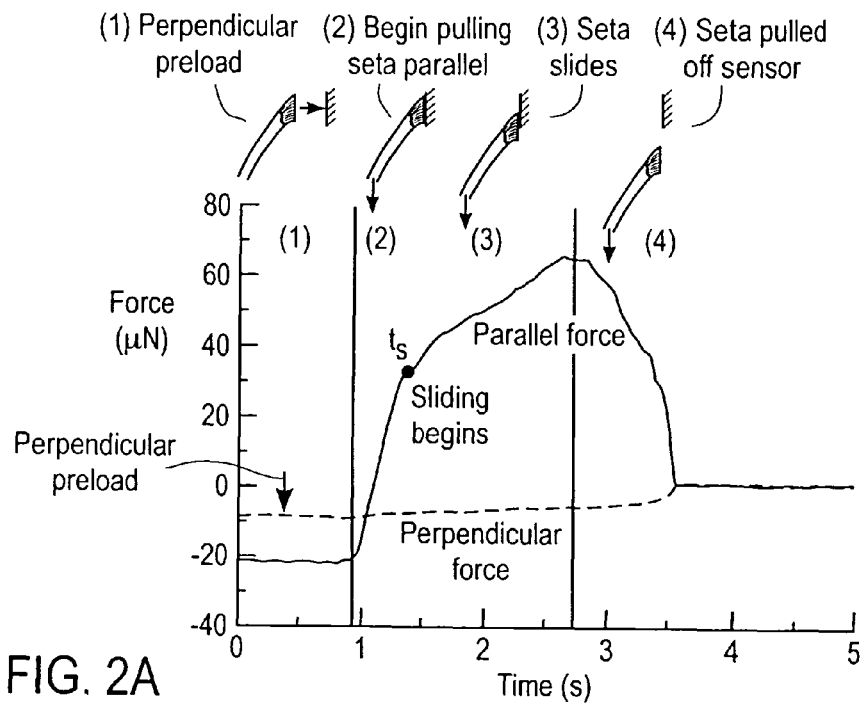
FIG. 2A-2B illustrate different forces, as a function of time, associated with the loading and adhesion operation of a structure of the invention.
Figure 2B:
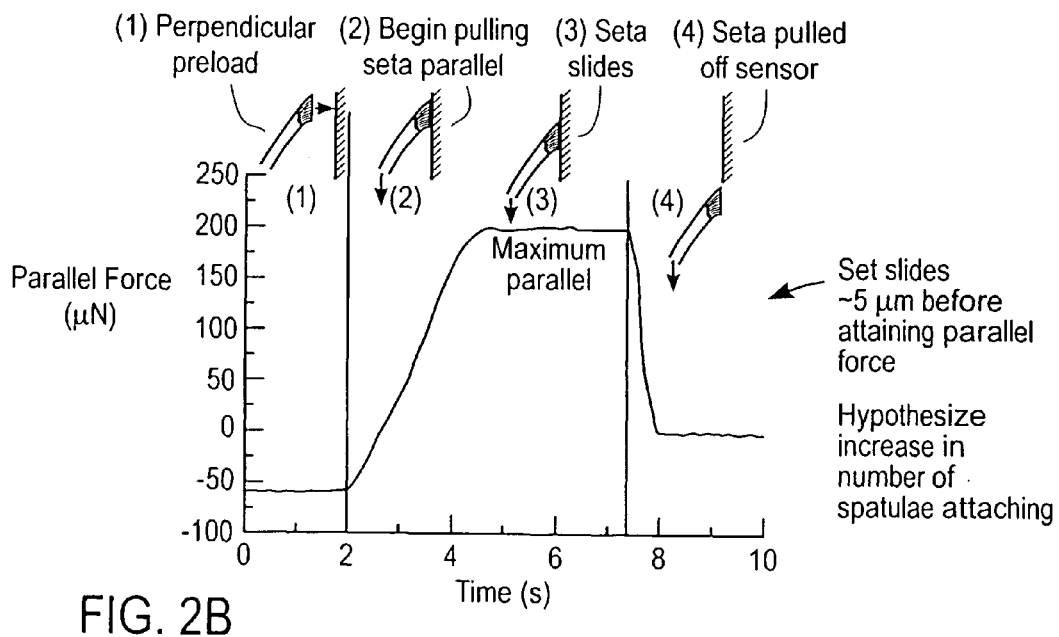
Figure 4:
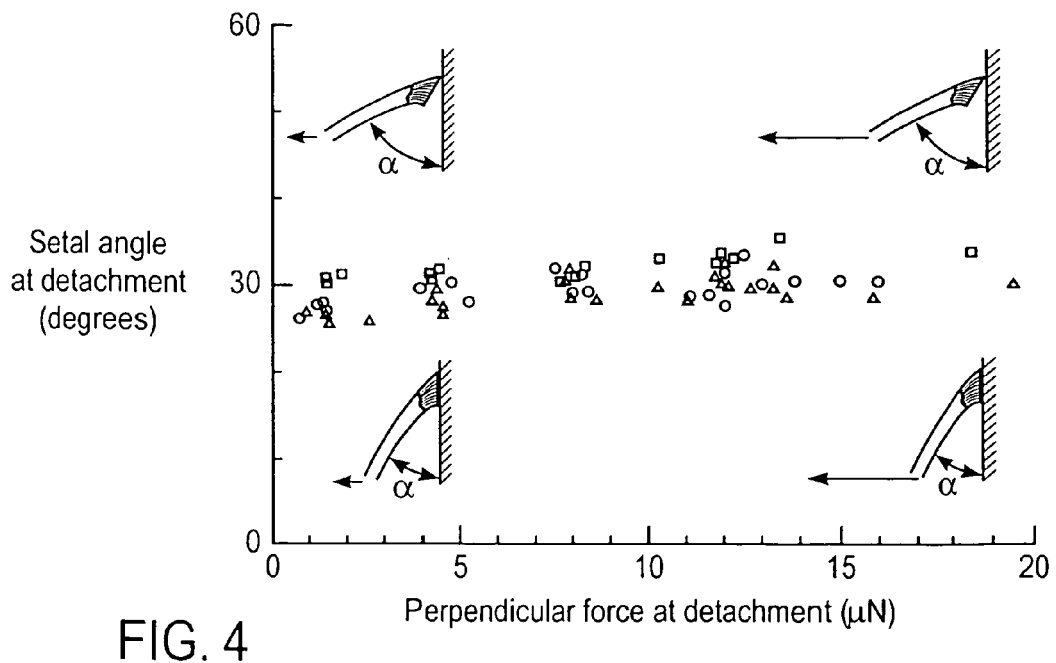
FIG. 4 illustrates perpendicular force during detachment of a structure utilized in accordance with the invention.

The results of these operations are shown in FIG. 2-4. FIG. 2A illustrates forces associated with a perpendicular preload and a subsequent parallel pulling performed in accordance with the invention. As shown in FIG. 2A, setal adhesive force parallel to the surface increased linearly until the seta began to slide off the edge of the sensor at time $t_x$. If the seta was allowed to slide approximately 5 μm along the sensor's surface, a distance imperceptible at the level of the foot, adhesive force continued to increase, as shown in FIG. 2B. The maximum adhesive force of single seta averaged 194 μN±25 SD (N=28), nearly 10-fold greater than predicted from whole animal estimates.

The single-seta force measurements suggest that if all setae were simultaneously and maximally attached, a single foot of a gecko could produce 100 N of adhesive force (−10 arm). Stated another way, the foot of a gecko could generate maximum observed force (10 N) with only 10% of its setae maximally attached.

The maximum force developed by a given seta could not be predicted from molecular interactions or microscopic anatomy alone. Setal force depended on its three-dimensional orientation (spatulae pointing toward or away from the surface) and the extent to which the hair was preloaded (i.e., pushed into and pulled along the surface) during initial contact Contacting the surface with the seta in a direction other than with spatulas projecting toward the surface resulted in forces less than 0.3 μN when the seta was pulled away perpendicular to the surface. A pull parallel to the surface showed that the force produced by the inactive, non-spatular region increased with normal or perpendicular force, typical of a material with a coefficient of friction equal to 0.25, see FIG. 3. By contrast, when the active spatular region was projecting toward the surface, force increased by 20 to 60-fold. The force resulting from pulling the seta parallel to the surface during attachment increased when setae were first pushed toward the surface providing a perpendicular preloading force, shown in FIG. 2A. This initial perpendicular force need not be maintained during the subsequent pull. Setal force parallel to the surface increased linearly with the perpendicular preloading force, as shown in FIG. 3. Experiments in which seta were pulled away from a surface (e.g., surface 40, a wire in FIG. 1F) demonstrated that perpendicular preloading alone is insufficient to prevent the seta from being dislodged easily. Seta that were first pushed into the surface and then pulled parallel to it developed over ten times the force (13.6 µN±2.6 SD; N=17) upon being pulled away from the surface than those having only a perpendicular preload (0.6 µN±0.7 SD; N=17). The largest parallel forces were observed only following a few microns of sliding, as shown in FIG. 23.

The results of preloading on setal force production support the hypothesis that a small perpendicular preloading force in concert with a rearward displacement or parallel preload may be necessary to "engage" adhesion. Since the tips of the setae are directed rearwards away from the toenail, preloading may increase the number of spatulae contacting the surface.

The orientation of the setae also appears to be important in detachment during locomotion. The force produced when a seta was pulled away from the surface was not significantly different from the force measured during a pull parallel to the surface if the same perpendicular preload was given. However, it was identified that setae detached at a similar angle (30.6°±1.8 SD; N=17) when pulled, away from the wire sensor's surface. To check for the presence of a critical angle of detachment, perpendicular force was held constant, while the setal angle ($\alpha$; FIG. 1F) progressively increased until detachment Setal angle at detachment changed by only 15% over a range of perpendicular forces, as shown in FIG. 4. This observation is consistent with an adhesive model where sliding stops when pulling at greater than the critical setal angle and hence stress can increase at a boundary, causing fracture of the contact. Change in the orientation of the setae and perhaps even the geometry of the spatulae may facilitate detachment.

It has long been known that geckos peel the tips of their toes away from a smooth surface during running. Toe peeling may have two effects. First, it may put an individual seta in an orientation or at a critical angle that aids in its release. Second, toe peeling concentrates the detachment force on only a small subset of all attached setae at any instant. The toe peeling behavior is analogous to the technique used by humans to remove a piece of tape from a surface.

The direct setal force measurements are consistent with the hypothesis that adhesion in geckos is the result of intermolecular forces. The simple models available can only give the most approximate estimates of setal force production. If it is assumed that the tip of a spatula is a curved segment of a sphere (radius, R=2 µm) and is separated by a small distance from a large, flat surface where van der Waals forces become significant (atomic gap distance, D=0.3 nm), then setal force=$AR/6D^2$, where A is the material dependent Hamaker constant taken to be $10^{-19}$ J[10]. This estimate puts the van der Waals force for a spatula to be about 0.4 µN. Since the number of spatula per seta varies from 100 to 1000, setal force estimates range from 40 to 400 µN.

Earlier experimental support for the van der Waals hypothesis comes from the observation that adhesive force of a whole gecko increases with increasing surface energy of the substrate. In addition, the rejection of alternative mechanisms such as suction, electrostatics, friction, microinterlocking, and wet adhesion, has been attempted. Adhesion experiments carried out in a vacuum and the disclosed measurements of greater than one atmosphere of adhesion pressure strongly suggest that suction is not involved. Experiments using X-ray bombardment eliminates electrostatic attraction as a mechanism necessary for setal adhesion, since the setae can still adhere in ionized air. Microinterlocking could function as a secondary mechanism, but the ability of geckos to adhere to polished glass shows that irregularities on the scale of the spatulae are not necessary for adhesion. The findings herein do not support a friction mechanism because the cantilever's surface is smooth (surface roughness less than or equal to 2.5 nm) and the coefficient of friction of the setal keratin on silicon is low ($\mu$=0.25; FIG. 3; dashed line). Capillary adhesion or glue are not likely mechanisms, since skin glands are not present on the feet of lizards. The mechanism of adhesion may involve a thin layer of water, or adsorbed water molecules on the seta and/or substrate.

Van der Waals forces are extremely weak at greater than atomic distance gaps, and require intimate contact between the adhesive and the surface. Polymeric adhesives such as tape are soft, and are able to deform sufficiently for intimate contact over a relatively large surface area. The feet of a Tokay gecko (Gekko gecko) contain approximately one billion spatulas that appear to provide a sufficiently large surface area in close contact with the substrate for adhesion to be the result of van der Waals forces.

Figure 5A:
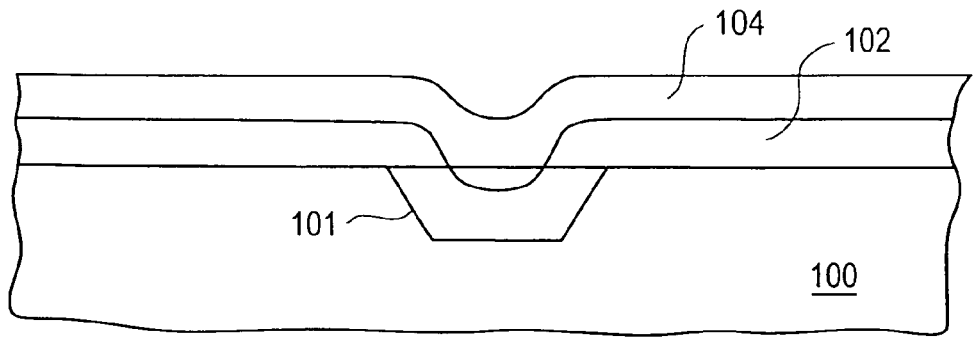
FIG. 5A-5C illustrate the fabrication of an array of setae with spatula structures in accordance with an oxide/nitride fabrication process utilized in accordance with an embodiment of the invention.
Figure 5B:
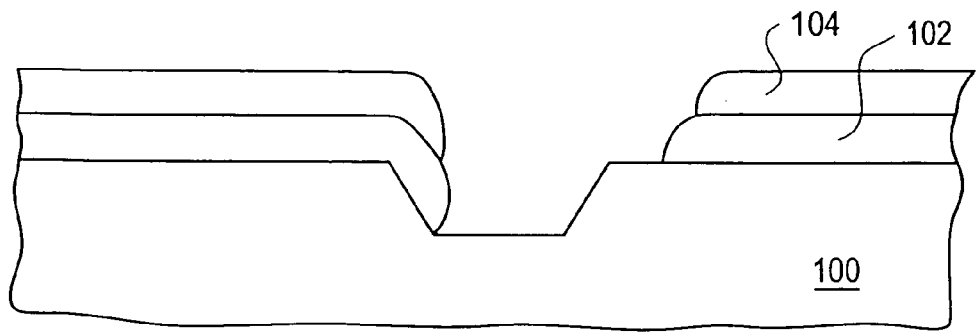

As previously indicated, the invention may be used in connection with setae harvested from a live specimen. Alternately, the techniques of the invention may be used in connection with fabricated setae. Those skilled in the art will recognize a number of techniques that may be used to fabricate setae in accordance with the invention. For example, the devices may be fabricated through an oxide/nitride process, as shown in FIGS. 5A-5C.

Initially, a recess is etched in a semiconductor substrate. FIG. 5A illustrates a recess 101 formed in a semiconductor substrate 100. Nitride and oxide layers are then deposited on the substrate 100. FIG. 5A illustrates a nitride layer 102 and an oxide layer 104. The surface is then patterned and etched, resulting in the structure of FIG. 5B.

Figure 5C:
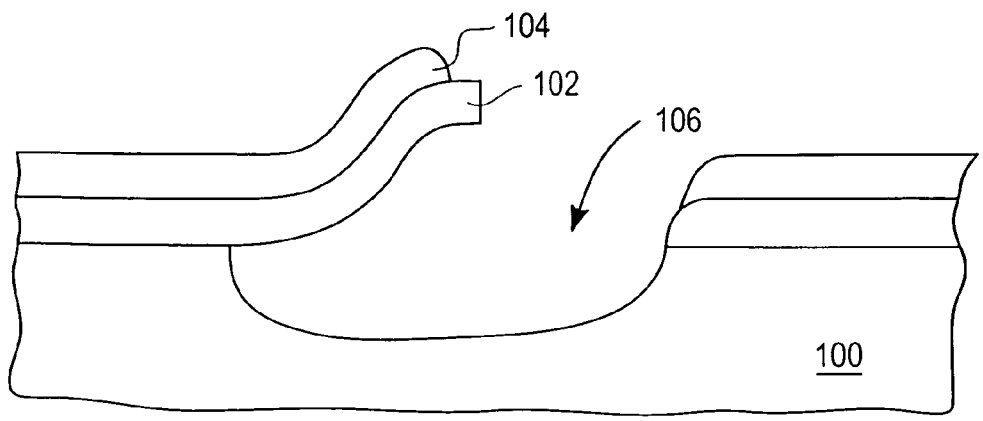

Afterwards, the underlying substrate 100 is etched, resulting in a well 106, as shown in FIG. 5C. At his point, the stress difference between the oxide and nitride layers causes the structure to curl from the plane defined by the substrate 100, thereby forming a shaft structure. The end of the shaft may then be roughened to form spatulae. For example, the spatulae may be formed by wet etching, radiation, plasma roughening, electrochemical etching, and the like. Alternately, a separate spatulae may be affixed to the shaft. Techniques for fabricating spatulas are discussed below.

Figure 6A:
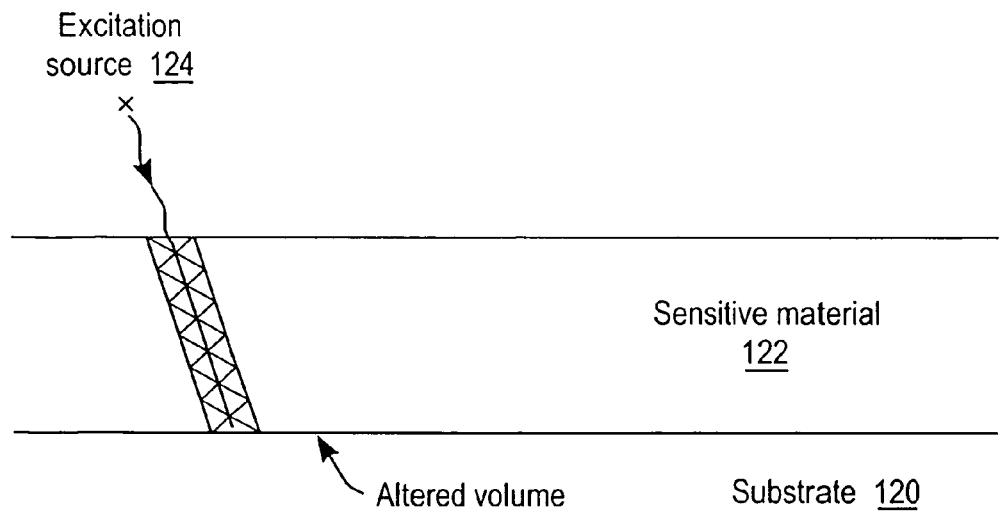
FIG. 6A-6B illustrate the fabrication of an array of setae in accordance with an excitation source process utilized in accordance with an embodiment of the invention.
Figure 6B:
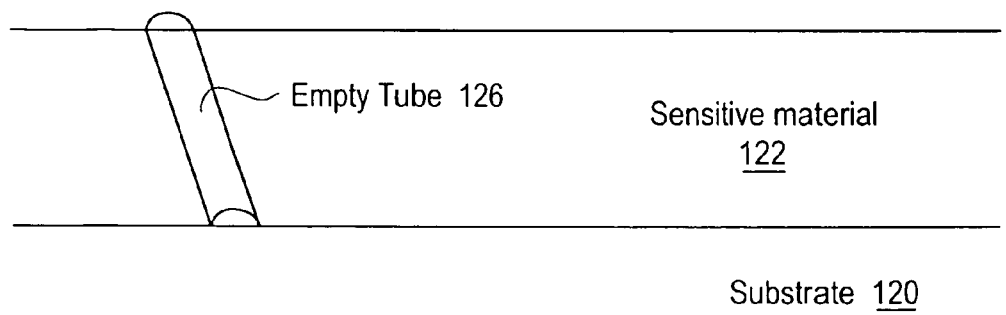

Another technique that may be utilized in accordance with the invention exploits an excitation source. As shown in FIG. 6A, a sensitive material 122 is formed on a substrate 120. An excitation source 124 is used to apply excitation energy to the sensitive material 122. The deep-penetrating excitation alters the volume along the trajectory of excitation. The altered vole is then selectively etched away. This results in a tube 126, as shown in FIG. 6B. At higher densities of exposure, the remaining material becomes a random array of isolated fingers. The end of each tube 126 is then processed to form spatulae or spatulae are attached to the tubes.

Figure 7:
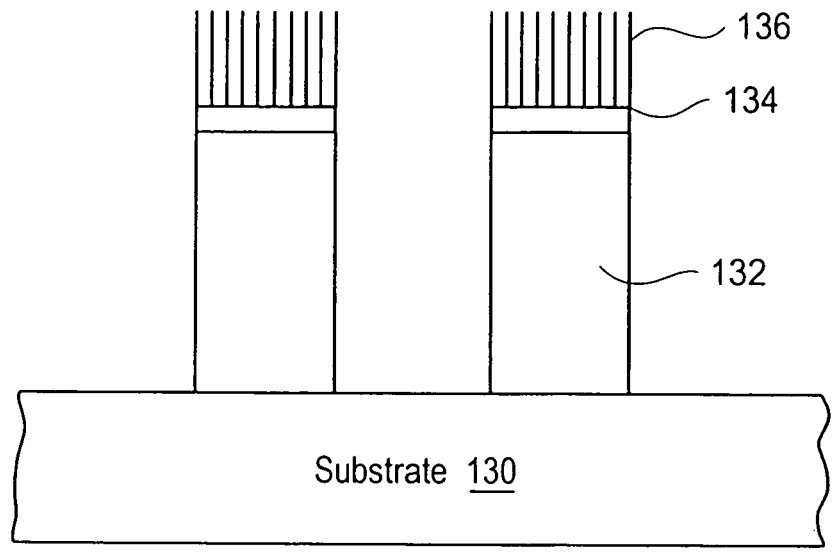
FIG. 7 illustrates the fabrication of an array of setae with spatula structures in accordance with a stalk and seeding process utilized in accordance with an embodiment of the invention.

FIG. 7 illustrates another technique that may be utilized in accordance with the invention. This embodiment relies upon the deposition of an etchable material on a substrate 130. Stalks 132 are then patterned and etched from the etchable material. The etched substrate may be coated with oxide and/or nitride layers. Alternately, polymer layers may be used as a coating. The polymer layers may be spin-cast, using materials, such as photoresist, polyimide, glass, or epoxy-based compounds. The resultant stalks 132 are then seeded to form nanotubes 136, operating as spatulae.

Figure 8:
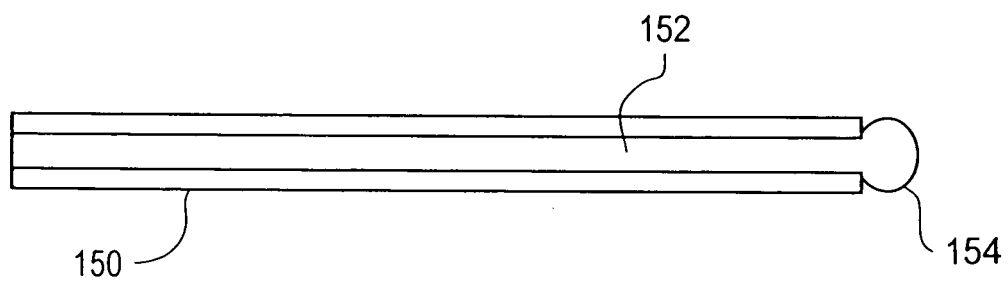
FIG. 8 illustrates the fabrication of a single spatula using a micro-pipette.

Artificial spatulas may be formed using a glass micro-pipette drawn down to a narrow aperture (e.g., 500 mm) at an end. Liquid polymer is extruded through the hollow pipette and is then cured. Surface tension creates a hemispherical drop at the end of the pipette. FIG. 8 illustrates this technique. In particular, the figure illustrates a micro-pipette 150 with a liquid polymer 152 positioned therein to form a hemispherical drop 154.

Materials that can be applied to the micro-pipette include low viscosity ultra violet cure epoxy, uncured silicone rubber, or polyurethane resin. The hemisphere at the end of the micro-pipette can be flattened or embossed by pressing against a polished surface. A flattened surface, such as the paddle structure of FIG. 1F, with its larger contact area, has better adhesive properties than a sphere.

The single spatula pipette can be used as an embossing tool to make a nano-mold by plastically deforming a material, such as molten polystyrene. A large area mold (e.g., 20 by 20 microns) can be formed by either step-and-repeat embossing or by making an array of pipettes and embossing a large pattern.

Figure 9:
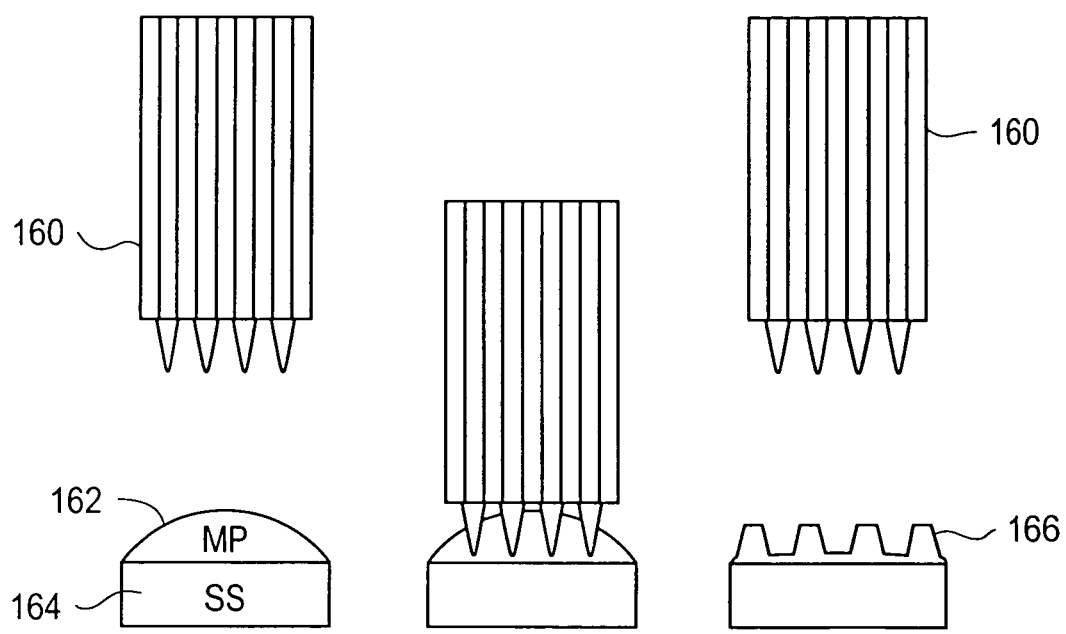
FIG. 9 illustrates an embossing tool used to form a spatulae mold for use in accordance with an embodiment of the invention.

FIG. 9 illustrates an array of pipettes used to form an embossing tool 160. The embossing tool 160 is applied to a polystyrene material 162 positioned on a substrate 164. This results in a patterned polystyrene surface 166.

Alternatively, a nano-channel glass, which consists of a large bundle of hollow glass fibers, can be used. The nano-channel glass can be filled with a polymer, and then the glass can be dissolved in an acid.

Spatulae may also be formed by lithographically induced self construction. With this technique, electrostatic attraction is used to pull liquid through a mask, and thereby "sprout" spatulae. This process is shown in connection with FIG. 10A-10D.

Figure 10A:
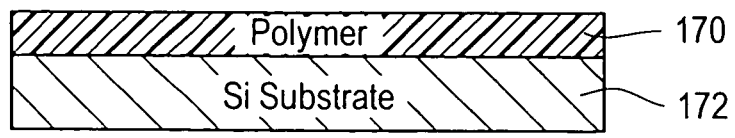
FIG. 10A-10D illustrate lithographically induced self-construction of spatulae in accordance with an embodiment of the invention.
Figure 10B:
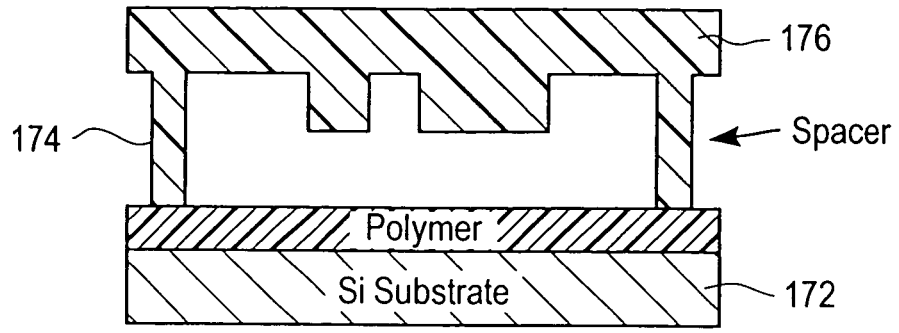
Figure 10C:
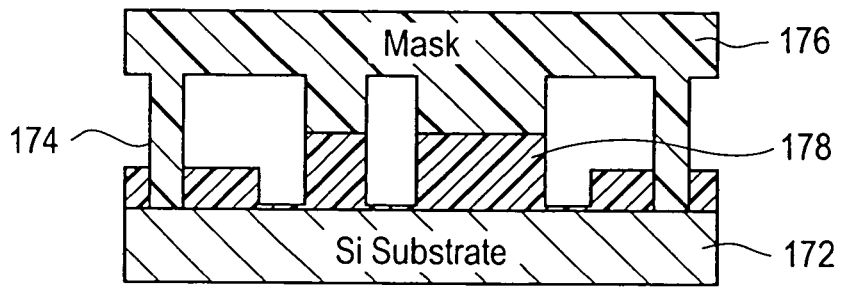
Figure 10D:
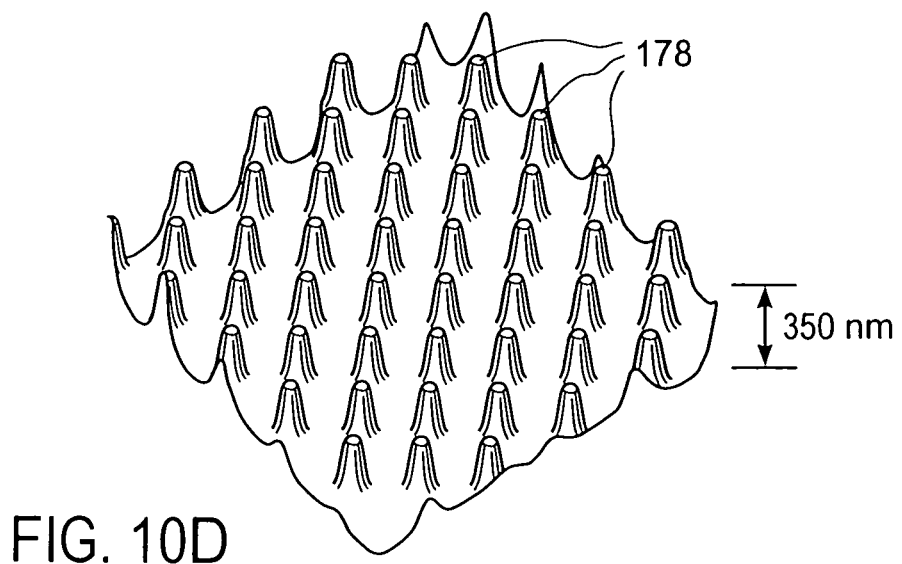

FIG. 10A illustrates a growing layer 170 positioned on a substrate 172. The growing layer may be molten polymer or thermoplastic. Spacers 174 are positioned on the substrate 172 and a mask 176 is constructed on the spacers 174. The growing layer 170 is electrostatically attracted to the upper mask layer 176, producing a set of protrusions 178, as shown in FIG. 10C. The resultant spatulae array is shown in FIG. 10D.

Figure 11A:
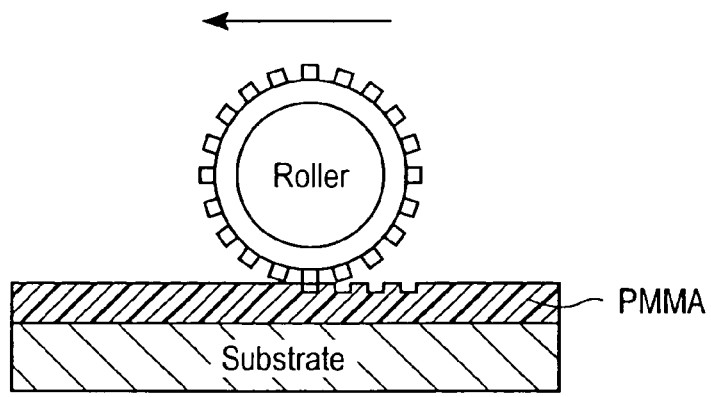
FIG. 11A-11B illustrate a roller nano-imprinting technique that may be used to form spatulae in accordance with an embodiment of the invention.
Figure 11B:
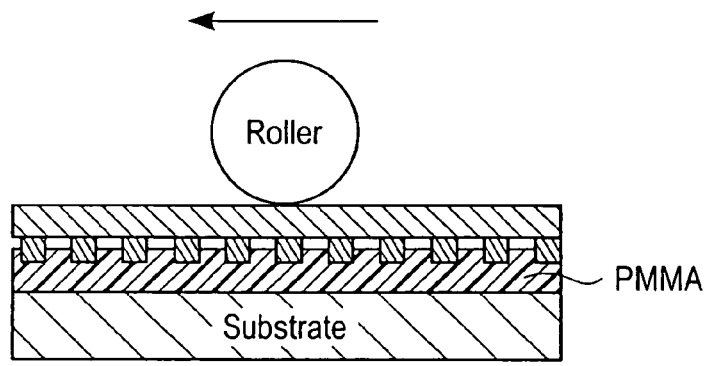

Stalks and spatulae may also be formed from a mold using a nano-imprinting roller. This technique is shown in connection with FIG. 11A-11B. While nano-imprinting techniques of the type shown in FIG. 11A-11B have been used in the prior art, they have not been used to produce spatulae structures.

Figure 12:
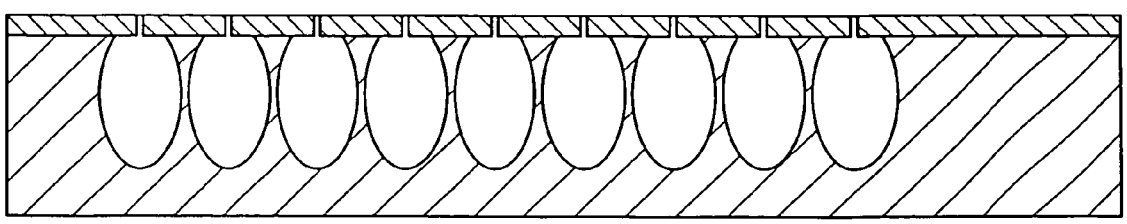
FIG. 12 illustrates a two-layer photoresist fabrication technique that may be used in accordance with an embodiment of the invention.

FIG. 12 illustrates that a 2-layer photoresists can be formed with different resist exposure sensitivities, so that the upper layer forms, for example, 100 nm square plates that are supported by much longer and thinner pedestals. Standing-wave interference patterns can be used to expose and pattern features to fabricate large area arrays. Similar structures can be made with SiOx layers on silicon substrates by plasma etching.

Setae shafts may be fabricated using a sandwich of polymer layers. A polymer layer can include spin-cast polymer materials, such as photoresist, polyimide, glass, or epoxy-based compounds. A polymer layer can also include spray-deposited polymer materials, such as photoresist, polyimide, glass, or epoxy-based compounds. Alternately, a polymer layer may be an ultra-violet curable epoxy.

Figure 13:
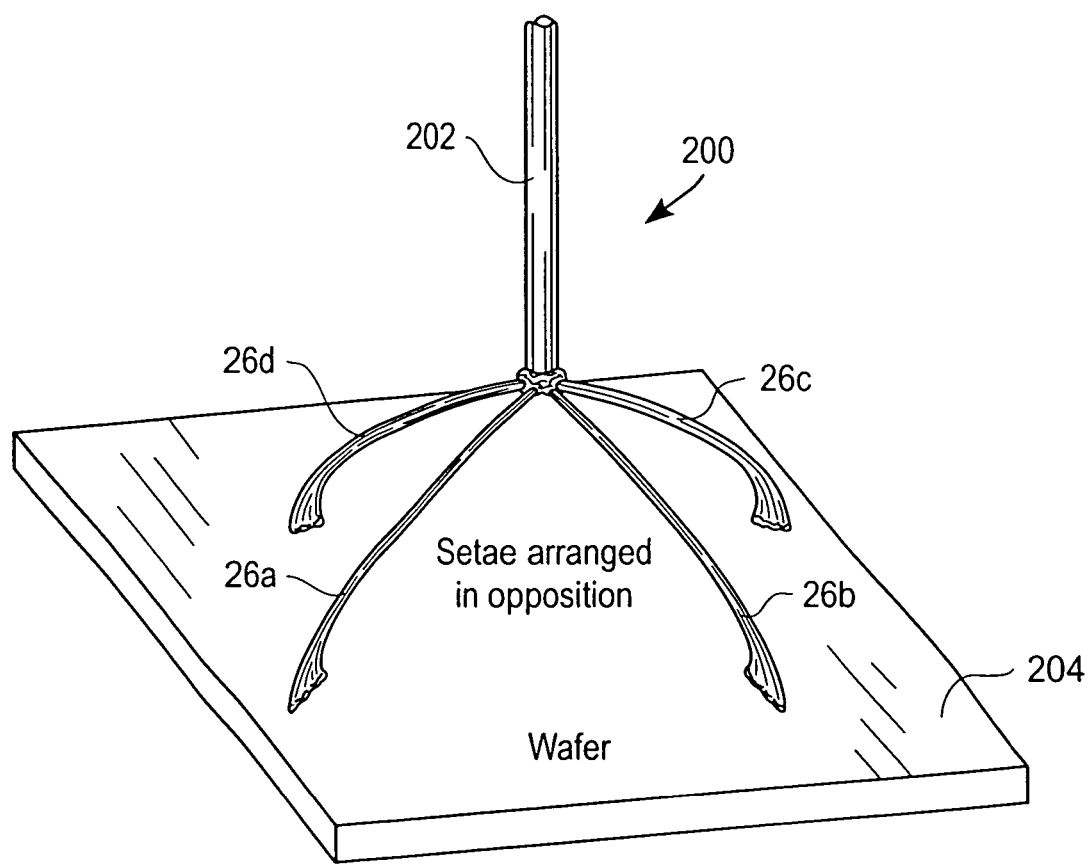
FIG. 13 illustrates a setae-based manipulator that may be used in accordance with an embodiment of the invention.

FIG. 13 illustrates a manipulator 200 formed in accordance with an embodiment of the invention. The manipulator 200 includes a beam 202 with a set of setae 26A-26D arranged in opposing pairs (e.g., 26A and 26C oppose one another, as do 26B and 26D). The beam 202 is pushed toward the substrate 204 to preload and spread the setae 26A-26D. The beam 202 is then pulled away from the substrate 204 to drag and pick-up the substrate 204. The beam 202 is pushed toward the substrate 204 to release the setae 26A-26D.

Those skilled in the art will recognize that the adhesive microstructures of the invention may be utilized in a variety of ways. For example, the technique of the invention can be used in pick and place micromanufacturing, micromanipulation, and microsurgery applications. For example, a seta can be attached to a micromanipulator to pick up a fiber optic, move it, and put it down again. Other uses include manipulating retinal prosthesis implants/explants, attaching to nerves during surgery, and pick and place of silicon wafers or disk drive components.

The setae of the invention may also be used as clutch mechanisms in micromachines. Since setae adhere in a directional manner, a seta could be used as a clutch mechanism similar to a ratchet, but on a smooth surface.

Other applications for the technique of the invention include: insect trapping, tape, robot feet or treads, gloves/pads for climbing, gripping, etc., clean room processing tools, micro-optical manipulation that does not scar a surface and leaves no residue or scratches, micro-brooms, micro-vacuums, flake removal from wafers, optical location and removal of individual particles, climbing, throwing, and sticker toys, press-on fingernails, silent fasteners, a substrate to prevent adhesion on specific locations, a broom to clean disk drives, post-it notes, band aids, semiconductor transport, clothes fasteners, and the like. In many of these applications, patches of spatula on a planar substrate are used, as opposed to patches of spatula positioned on a shaft.

Figure 14:
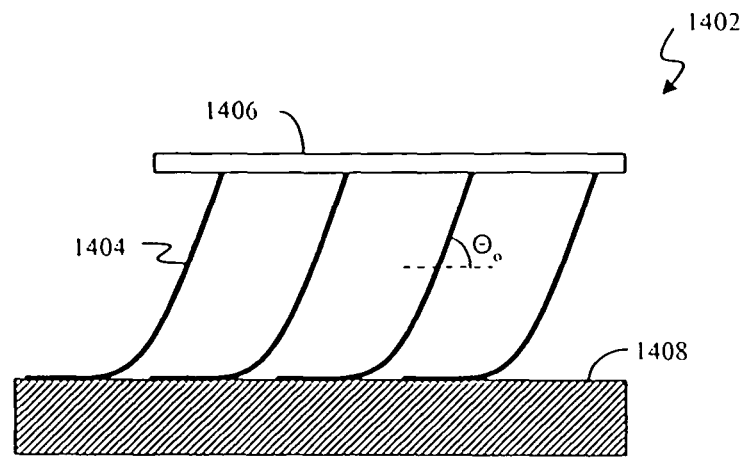
FIG. 14 illustrates a fabricated micron-sized structure with nano-structures disposed on a base.

With reference to FIG. 14, a fabricated micron-scale structure 1402 is depicted with a plurality of nano-structures 1404 attached to a base 1406. In one exemplary embodiment, nano-structures 1404 are seta structures, and base 1406 is a substrate, which can be rigid or flexible. Thus, in this exemplary embodiment, FIG. 14 depicts seta structures, disposed on a substrate, adhering to contact surface 1408 using intermolecular forces, and, in particular, van der Waals forces.

As described above, a seta structure has a shaft with an end that adheres to contact surface 1408. As also described above, the end of the shaft that adheres to contact surface 1408 can have essentially the same shape as the shaft, or can have one or more spatula structures, which may be in the form of a paddle or flattened surface, a flattened segment of a sphere, an end of a cylinder, a sphere, a blunt end, a bent cylinder, or any suitable shape.

In another exemplary embodiment, nano-structures 1404 are spatula structures, and base 1406 is a seta structure. Thus, in this exemplary embodiment, FIG. 14 depicts spatula structures, disposed on a seta structure, adhering to contact surface 1408 using intermolecular forces, and, in particular, van der Waals forces.

Figure 15:
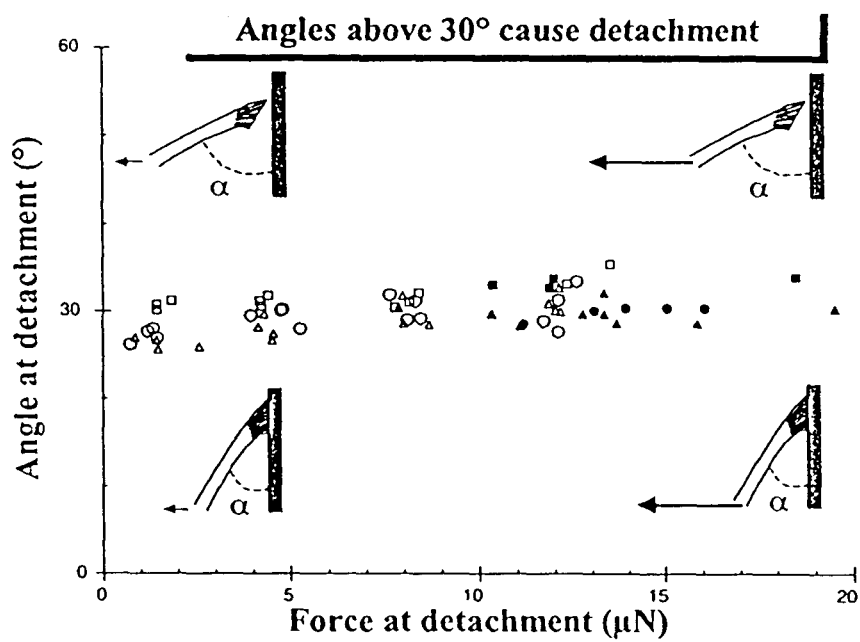
FIG. 15 illustrates the results of an experiment to measure the force of detachment of a seta.

As described above, with reference to FIG. 1I, a single seta of a Tokay gecko is depicted engaged with an aluminum wire used as a force gauge. With reference to FIG. 15, results of an experiment are depicted where the force of detachment was measured for various angles of detachment of the seta. As depicted in FIG. 15, contact was broken when the seta was pulled at an angle greater than 30 degrees relative to the contact surface. (See, K. Autumn, Y. Liang, T. Hsieh, W. Zesch, W.-P. Chan, T. Kenny, R. Fearing, and R. J. Full, adhesive Force of a Single Gecko Foot-Hair", Nature, vol. 405, pp. 681-685 (Jun. 8, 2000).)

1. Nano-Structure Design for Minimum Peel Strength

Figure 16:
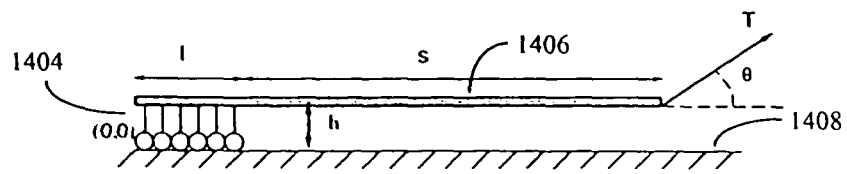
FIG. 16 illustrates a fabricated micron-sized structure with nano-structures disposed on a portion of a base.

With reference to FIG. 16, in one exemplary embodiment, base 1406 includes nano-structures 1404 attached at one portion of base 1406. It should be recognized that nano-structures 1404 can be a single structure or a plurality of structures, such as plates or spheres. In the present exemplary embodiment, when nano-structures 1404 adhere to contact surface 1408 and an external force is applied to peel base 1406 from contact surface 1408, nano-structures 1404 are disposed on a portion of base 1406 located at a distance away from where the external force acts such that the distance defines a moment arm for the applied external force to peel base 1406 from contact surface 1408.

In particular, assume that base 1406 can be modeled as a rigid beam, and neglect geometry changes due to bending. While a compliant base 1406 would slightly change the magnitudes, the overall results would be similar. As depicted in FIG. 16, a portion l of the overall length of base 1406 includes nano-structures 1404, while a portion s does not include nano-structures 1404. Thus, the overall length of base 1406 is (l+s). Assume that all of nano-structures 1404 are in contact with contact surface 1408 with a uniform adhesive pressure of $P_o Nm^{-1}$. As depicted in FIG. 16, height h corresponds to the height of nano-structures 1404. Assume a Coulomb friction model with coefficient of friction $\mu$, and $F_f = \mu F_n$.

Now assume a force T acts at angle $\theta$ to pull base 1406 off contact surface 1408. There are three possible conditions: sliding, lifting, and pivoting.

Sliding is characterized by equation (1):

$$T \cos \Theta > \mu(P_o l - T \sin \Theta). \tag{1}$$

Lifting is characterized by equation (2):

$$T \sin \Theta > P_o l. \tag{2}$$

Pivoting is characterized by equation (3):

$$T(s+l)\sin\theta > Th\cos\theta + \int_0^l P_o x \, dx, \tag{3}$$

or, for a particular angle $\theta$:

$$T > \frac{P_o l^2}{2} \frac{1}{(s+l)\sin\theta - h\cos\theta}. \tag{4}$$

Figure 17:
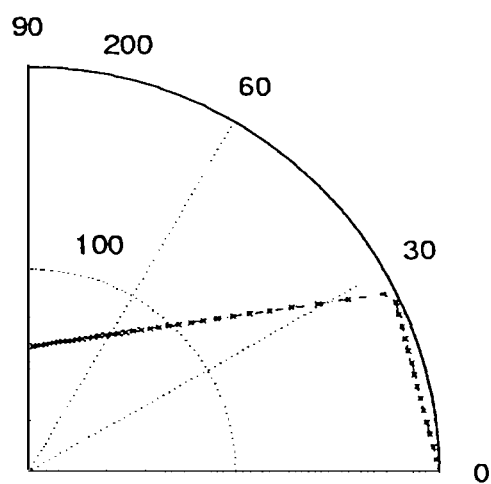
FIG. 17 illustrates the maximum pure tensile force needed before a nano-structure slides or peels.

As depicted in FIG. 17, for pull angles of less than approximately 30°, the nano-structure slides on the contact surface. FIG. 17 depicts the maximum pure tensile force T (in µN) before sliding or peeling, with $P_o=800$ µN, l=200 µm, s=110 µm, µ=0.25, and h=20 µm. As depicted in FIG. 17, for angles greater than 30°, the nano-structure peels off, with the force required for peeling dropping dramatically at higher pulling angles. The nano-structure can stand three times more load in shear than in the normal direction.

With reference again to FIG. 16, as described above, in one exemplary embodiment, nano-structures 1404 are seta structures, and base 1406 is a substrate. Thus, in this exemplary embodiment, FIG. 16 depicts seta structures disposed on one portion of a substrate.

As also described above, the end of a seta structure that adheres to contact surface 1408 can have essentially the same shape as the shaft of the seta structure, or can have one or more spatula structures. If the end of the seta structure has multiple spatula structures, the spatula structures can be oriented in the same direction or in opposing directions.

In another exemplary embodiment, nano-structures 1404 are spatula structures, and base 1406 is a seta structure. Thus, in this exemplary embodiment, FIG. 16 depicts spatula structures disposed on one portion of a seta structure.

2. Nano-Structure Design for Maximum Peel Strength

Figure 18:
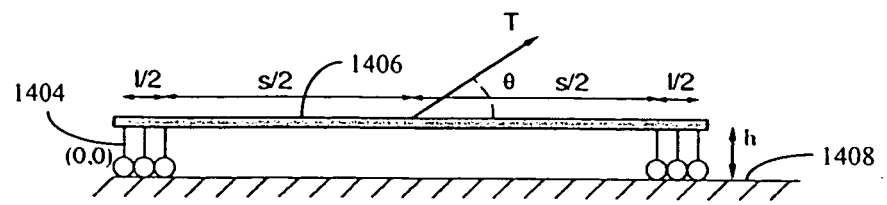
FIG. 18 illustrates a fabricated micron-sized structure with nano-structures disposed on portions of a base in opposing locations on the base.

With reference to FIG. 18, in another exemplary embodiment, base 1406 includes at least one nano-structure 1404 attached at opposing locations on base 1406. Thus, in the present exemplary embodiment, when nano-structures 1404 adhere to contact surface 1408 and an external force is applied to peel base 1406 from contact surface 1408, nano-structures 1404 located at opposing locations on base 1406 resist torque resulting from the applied external force.

In particular, assume a force T acts at angle $\theta$ in the middle of base 1406 to pull base 1406 away from contact surface 1408. Again, there are three possible conditions: sliding, lifting, and pivoting.

The sliding force T is the same as in equation (1), and the lift off force T is the same as in equation (2). Pivoting, however, can be characterized by equation (5):

$$T(s+l)\sin\theta > Th\cos\theta + \int_0^{l/2} P_o x \, dx + \int_{s+l/2}^{s+l} P_o x \, dx, \tag{5}$$

or, for a particular angle $\theta$:

$$T > \frac{P_o l(s+l)}{2} \frac{1}{\frac{s+l}{2}\sin\theta - h\cos\theta}. \tag{6}$$

Figure 19:
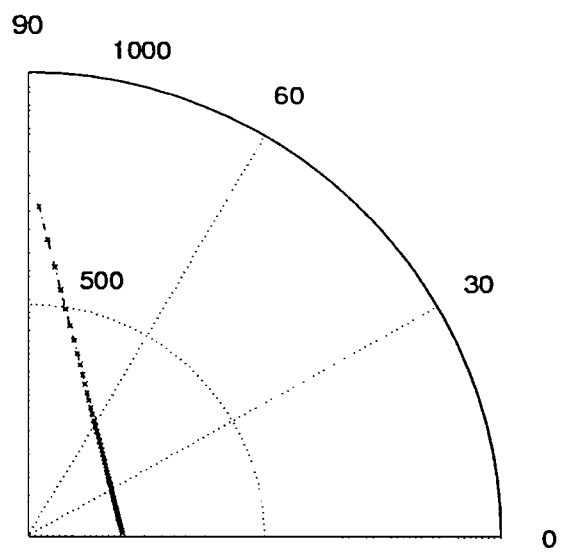
FIG. 19 illustrates the maximum pure force needed before a nano-structure slides or peels.

As depicted in FIG. 19, as compared to FIG. 17, the shear strength remains the same (200 µN) at $\theta=0°$, but the nano-structure slide rather than peel. As compared to FIG. 17, pulloff force at $\theta=90°$ is an order of magnitude higher for the same adhesive force at the nano-structure and the same dimensions.

Thus, with reference to FIGS. 16 and 18, one or more nano-structures 1404 can be located on portions of base 1406 to facilitate or inhibit peeling of base 1406 from contact surface 1408. In particular, with reference to FIG. 16, to facilitate peeling, one or more nano-structures 1404 are disposed on base 1406 in a location to produce torque from an applied external force. With reference to FIG. 18, to inhibit peeling, nano-structures 1404 are disposed on base 1406 in opposing locations to resist torque from an applied external force.

In other exemplary embodiments, various geometric shapes and patterns of nano-structures can be used. For example, radially oriented nano-structures can provide resistance to peel off in all directions. In addition, suction-cup like structures covered with nano-structures can be used to engage the nano-structures in a radial direction. Such a suction cup-like structure would not rely on vacuum for adhesion, and thus such a device would stick underwater or in vacuum.

With reference again to FIG. 18, as described above, in one exemplary embodiment, nano-structures 1404 are seta structures, and base 1406 is a substrate. Thus, in this exemplary embodiment, FIG. 18 depicts seta structures disposed on opposing locations on a substrate to resist torque from an applied external force. For example, as described above, FIG. 13 depicts a set of setae 26A-26D (seta structures) arranged in opposing pairs on beam 202 (substrate).

With reference again to FIG. 18, as also described above, the end of a seta structure that adheres to contact surface 1408 can have essentially the same shape as the shaft of the seta structure, or can have one or more spatula structures. If the end of the seta structure has multiple spatula structures, the spatula structures can be oriented in the same direction or in opposing directions.

In another exemplary embodiment, nano-structures 1404 are spatula structures, and base 1406 is a seta structure. Thus, in this exemplary embodiment, FIG. 18 depicts spatula structures disposed on opposing locations on a seta structure to resist torque from an applied external force.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

We claim:

1. A fabricated microstructure, comprising:
a substrate; and
an array of seta structures configured to adhere to a contact surface by van der Waals forces between the array of seta structures and the contact surface, wherein the array of seta structures are disposed on the substrate in opposing orientation to resist peeling when the array of seta structures adhere to the contact surface.

2. The fabricated microstructure of claim 1, wherein each seta structure of the array of seta structures include one or more spatula structures disposed on one or more portions of each seta structure of the array of seta structures, and wherein the one or more spatula structures adhere to the contact surface by van der Waals forces.

3. The fabricated microstructure of claim 2, wherein spatula structures disposed on each seta structure of the array of seta structures are oriented in the same direction or opposing directions.

4. A fabricated microstructure, comprising:
a substrate; and
an array of seta structures configured to adhere by van der Waals forces to a contact surface by van der Waals forces between the array of seta structures and the contact surface, wherein the array of seta structures are disposed on the substrate in opposing orientation to resist peeling when the array of seta structures adhere to the contact surface;
wherein the array of nano-structures is configured to adhere to a contact surface by van der Waals forces between the array of nano-structures and the contact surface, and without a microinterlocking structure disposed on the contact surface.

5. The fabricated microstructure of claim 1, wherein the an array of seta structures is configured to adhere to a contact surface by van der Waals forces between the array of seta structures and the contact surface, and without a microinterlocking structure disposed on the contact surface.

* * * * *